(12) United States Patent
Dombrowski

(10) Patent No.: US 7,509,956 B2
(45) Date of Patent: Mar. 31, 2009

(54) SECURE AIRWAY CLIP

(76) Inventor: John F. Dombrowski, 5123 Watson St. NW., Washington, DC (US) 20016

( * ) Notice: Subject to any disclaimer, the term of this patent is extended or adjusted under 35 U.S.C. 154(b) by 524 days.

(21) Appl. No.: 10/891,505

(22) Filed: Jul. 15, 2004

(65) Prior Publication Data
US 2005/0034729 A1 Feb. 17, 2005

Related U.S. Application Data

(60) Provisional application No. 60/487,286, filed on Jul. 16, 2003.

(51) Int. Cl.
*A62B 9/04* (2006.01)
(52) U.S. Cl. .............. 128/202.27; 128/200.26; 128/207.14; 128/207.15; 128/207.16; 439/368; 439/369; 403/335; 403/286; 403/294; 403/338; 403/341; 24/563; 285/319; 285/320; 285/308
(58) Field of Classification Search ............... 128/912, 128/207.14, 207.15, 207.16, 207.17, 200.26; 439/368, 369; 403/286, 294, 335, 338, 341; 24/563, DIG. 31, DIG. 52; 285/319, 320, 285/308
See application file for complete search history.

(56) References Cited
U.S. PATENT DOCUMENTS

| | | | |
|---|---|---|---|
| 4,248,236 A * | 2/1981 | Linder | 604/100.01 |
| 4,852,564 A * | 8/1989 | Sheridan et al. | 128/202.27 |
| 4,997,421 A * | 3/1991 | Palsrok et al. | 604/174 |
| 5,388,575 A | 2/1995 | Taube | |
| 6,055,984 A | 5/2000 | Brain | |
| 6,186,561 B1 * | 2/2001 | Kaishio et al. | 285/319 |
| 6,484,724 B1 | 11/2002 | Sloan | |
| 6,761,165 B2 | 7/2004 | Strickland, Jr. | |
| 6,761,171 B2 | 7/2004 | Toti et al. | |

OTHER PUBLICATIONS

ASTM Standard F 1590-95, "Standard Specification for Tracheostomy Tube Connectors", An American National Standard, ASTM International, Annual Book of ASTM Standards, vol. 13.01:942-943 (1995).
ASTM Standard F 1243-89 (Reapproved 1995), "Standard Specification for Tracheal Tube Connectors", An American National Standard, ASTM International, Annual Book of ASTM Standards, vol. 13.01:565-567 (1990).

* cited by examiner

*Primary Examiner*—Patricia Bianco
*Assistant Examiner*—Nihir Patel
(74) *Attorney, Agent, or Firm*—Perry E. Van Over & Associates PLLC

(57) ABSTRACT

Provided is a device for attachment to tubular connections that serves to ensure the securing of the connection and the avoidance of inadvertent disconnections. Also provided is an endotracheal tube having a releasable locking device component that serves to ensure security of the connection of the endotracheal tube to a breathing system. Also provided is a breathing system having a releasable locking device component that when employed ensures the security of the connection.

9 Claims, 7 Drawing Sheets

SECURE AIRWAY CLIP

This application claims priority from U.S. Provisional Application Ser. No. 60/487,286 filed Jul. 16, 2003. The entirety of that provisional application is incorporated herein by reference.

BACKGROUND OF THE INVENTION

1. Field of the Invention

This invention relates generally to medical devices and anaesthesiology products, and particularly to an improved system for the secure inter-connection of tracheal tubes.

2. Background of the Technology

Endotracheal tubes are used regularly in hospitals around the world as an essential gas conduit when patients undergo anesthesia. The use of these devices has become widely accepted throughout the medical community and their design has become very standardized over the past twenty years with little change or improvement.

The distal end of the tracheal tube, that which projects outward from the patient, is commonly referred to as the machine end of the endotracheal tube. The machine end terminates in a connector for attachment to a breathing circuit or system. These endotracheal tube connectors have also become very standardized, and incorporate male-to-female conical tapers, that are intended to releasably but securely lock together relying on the friction fit of the tapered male-to-female connectors. While this friction fit connector allows ease of connection and disconnection it also permits the inadvertent disconnection of the breathing system from the tracheotomy tube. This inadvertent disconnection of the endotracheal tube from the breathing system during a surgical procedure is a well-recognized hazard that prior to the present invention was not well addressed in the medical community.

While attempts have been made to address the hazard of inadvertent disconnection of the endotracheal tube, the results have been largely unsuccessful. In addressing this issue, the medical profession refers to the hazard of inadvertent disconnection of the endotracheal tube in general terms in the ASTM standard F1590-95. In this publication, which is fully incorporated herein by reference, allowance is made for the addition of a mechanism to make a more secure attachment between the conical fittings, if so desired, suggesting a remedy in the form of retaining or locking devices such as hooks, lugs or studs. No specific design or guidance to arrive at a design is provided. An additional ASTM standard, F1243-89, which is fully incorporated herein by reference, makes reference to lugs, knobs or other projections that can be used to attach elastic bands to the connectors to resist accidental separation. For want of a more reliable means to releasably secure the tapered male-to-female connectors for endotracheal tubes, many hospitals have simply relied on this makeshift remedy of wrapping elastic bands around the connection.

More recently a new design for an endotracheal connector has been suggested by Sloan, U.S. Pat. No. 6,484,724. This device uses two concentric tapers to lock the endotracheal tube to the breathing system. The device of Sloan requires an entirely new design for the machine end of the endotracheal tube and therefore is incapable of being retrofitted to the existing worldwide inventory of endotracheal tubes and the endotracheal tubes that are currently in production. Further, the design of two concentric tapers provided by the Sloan device does nothing to remedy the fact that security of the connection is still solely reliant on a friction fit a male-to-female type connector. For this reason, an urgent need still exist in the medical art for a releasable means to ensure the security of currently used male-to-female connectors of the machine end of an endotracheal tube to a breathing system.

SUMMARY OF THE INVENTION

It is the general object of the present invention to provide a simple mechanical device which can be releasably attached to the inter-connected tubes in the proximity of the connectors to secure the connection and prevent the inadvertent disconnection of the tubes.

It is a further object of this invention to provide a universal locking device which facilitates the rapid assembly and releasable locking of connections between two tubes in a controlled, predictable manner.

It is a further object of this invention to provide a releasable connector locking device adapted to secure the machine end of an endotracheal tube to a breathing system.

It is a further object of this invention to provide an endotracheal tube having a releasable locking mechanism that secures the connection of the machine end of an endotracheal tube to a breathing system.

It is a further object of this invention to provide the releasable locking mechanism as a component of a kit that is provided in as sterile package for operating room use; the kit including at least one locking device of at least one size and configuration as well as endotracheal tubes of varying sizes with accompanying connectors for use with a breathing system.

It is a further object of this invention to provide a breathing system having a releasable connection locking device that secures the connection of the breathing system to the machine end of an endotracheal tube.

DETAILED DESCRIPTION OF THE INVENTION

Figure 1:
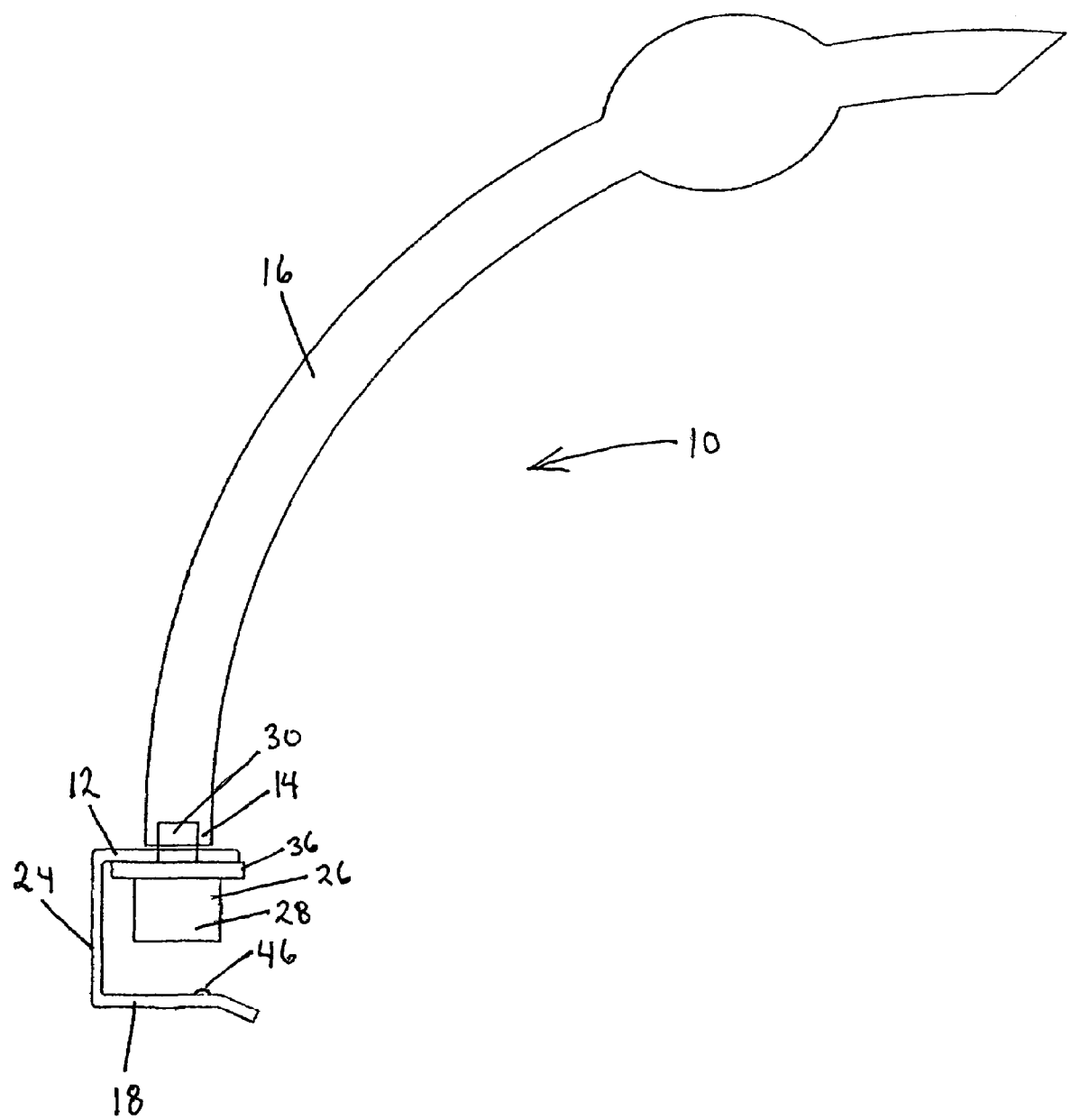
FIG. 1 provides a planar view of an endoscopic tube with the device of the present invention operationally positioned at the machine end of the endoscopic tube.

The present invention is described by the following detailed description and the accompanying figures of a non-limiting example of a releasable mechanical device for securing the machine end of an endotracheal tube to a breathing system. It is understood that the present invention is not limited to securing such connections but can be easily applied to releaseably securing any tube connector to a corresponding receiving connector without departing from the concept of the invention.

As best shown in FIGS. 1-7, the present invention is a releasable locking device, generally shown at (10), that is sized and configured to have a first end (12) of the device (10) disposed at least partially around or adjacent to a first end (14) of a tubular structure (16). The device (10) is preferably manufactured of a resilient material such as surgical instrument grades of stainless steel, however, any resilient material that is strong, flexible, and has good memory shape will suffice; to include plastics, or any shape memory or super-elastic alloy such as Nickel-titanium (Nitinol), for example. A second end (18) of the device (10) is sized and configured to releasably circumvent at least a portion of a first end (20) of a second tubular structure (22). Connecting the first end (12) and the second end (18) of the device (10) is a bridging member (24). The device (10) can be configured such that the first end (12) and the second end (18) of the device (10) are substantially parallel one to the other and the bridging member (24) connecting the first end (12) and the second end (18) of the device (10) is disposed substantially perpendicular to both ends (12, 18). As so configured and as best shown in FIGS. 1-4 and 6, one embodiment of the device from a side view can be seen as being essentially in the shape of 3 sides connected by approximate 90° angles. This exemplary locking device (10) is configured for two connectors, which join to each other along a common central axis. However, the present invention is not so limited by this example and can be modified to conform to connectors which are joined at other than right-angles one to the other. It is also within the concept of the present invention for the bridging member (24) to be arched rather than planar without departing from the concept of the present invention.

The present invention can be used to provide a releasable locking device to protect against inadvertent disconnection of any two hoses connected together. The following description of the device in combination with an breathing system connected to an endotracheal tube is provided as a non-limiting example. The connections between the breathing system (56) and the endotracheal tube (16) can employ a variety of male-to-female type connectors. The breathing system (56), as is well known in the art with its connector and necessary tubular or hose connections (a breathing system assembly) can vary from the following description without departing from the concept of the present invention. Similarly, the endotracheal tube with its connector and included elements (an endotracheal tube assembly) can vary from the provided description without departing from the present concept.

In the following example, the connection is made between the first end (machine end) (14) of a first tubular structure (16) (an endotracheal tube) to the first end (20) of a second tubular structure (breathing system tube) (20). The first connector (26) is configured to have a first connector female end (28) and a first connector male end (30), which are connected by a first connector central body (32), all of which share a common first connector lumen (34) through which gases can pass into, through, and out of the first connector (26). Circumferentially disposed around at least a portion of the first connector central body is a first connector retaining structure (36). Preferably this retaining structure (36) is configured as a complete ring or flange that encircles the central body (32) although partial encirclement of the central body will suffice. The first connector male end (30) is sized and configured to snugly fit within the lumen (38) of the first tubular structure (16), which in the present example is the lumen of the machine end of an endotracheal tube. The first connector female end (28) is sized and configured to receive a male end (40) of a second connector (42). This second connector (42) is secured to the first end (20) of the second tubular structure (22). In the present example, this second tubular member (22) is the tube or hose that extends from the breathing system for the purpose of connection to an endotracheal tube. Similar to the operational relationship between the first connector (26) and the first tubular structure (16), described above, the second connector (42) and the second tubular structure (22) can be releasably connected such that the user can, if desired, disconnect the first connector (26) or second connector (42) from their respective first or second tubular structures (16, 20). It is also within the concept of the present invention that the first or second connectors (26, 42) can be fixedly connected to their respective first or second tubular structures (16, 20). Such a connection can be accomplished as part of the manufacturing process of either the first tubular structure or the second tubular structure. For example, as shown in an alternative embodiment in FIG. 6, the circular or first end (12) of the device (10) can be assembled about the circumference of the second tubular structure during the manufacturing process; that is, for example, the breathing system can include the device (10) as part of the breathing system tube assembly from the manufacturer. It is also within the scope of the present invention that the device (10) can be assembled on the first end (14) of the first tubular structure (16) during the manufacturing assembly process; that is in the above provided example, an endotracheal tube could be provided from the manufacturer with the device (10) already assembled as a component of the endotracheal tube from the manufacturer.

Figure 2:
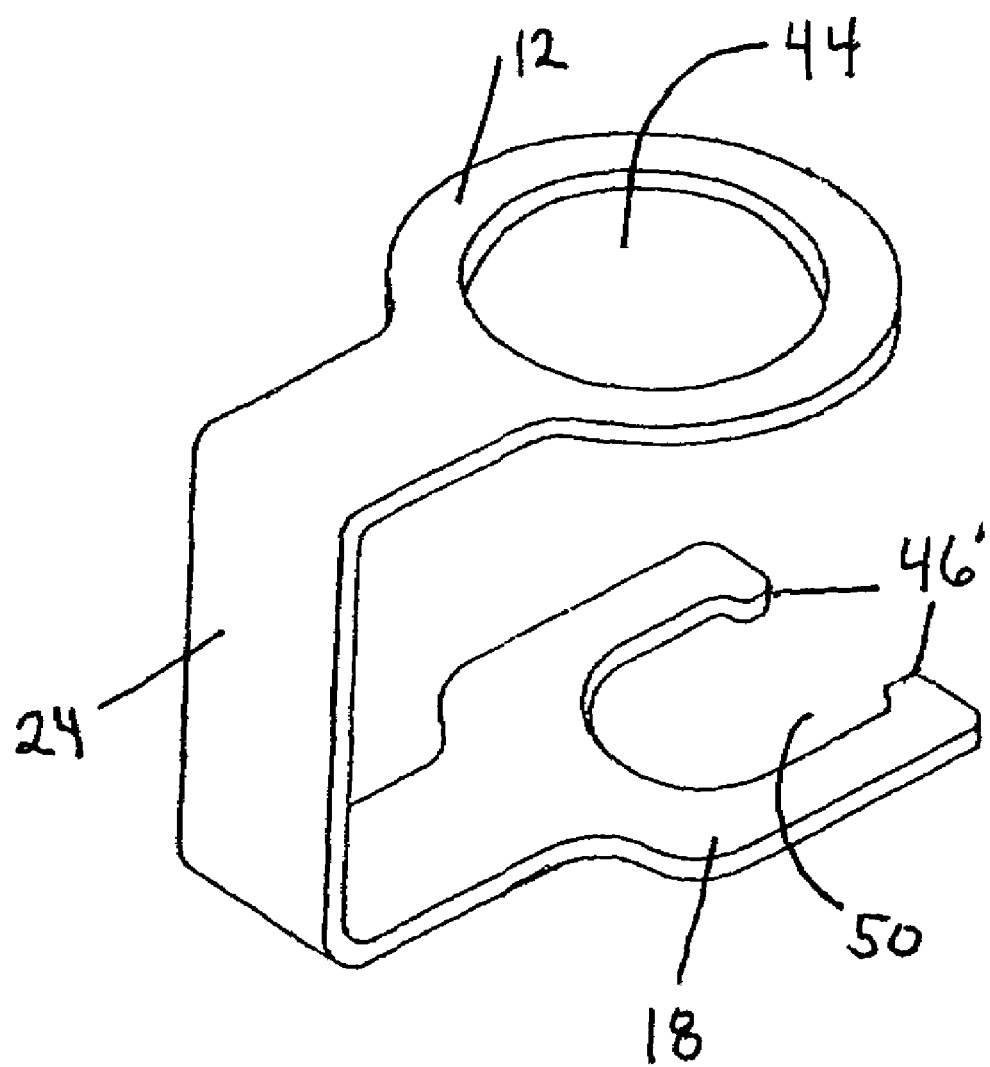
FIG. 2 provides a perspective view of the device of the present invention as seen from the outer surface of the bridging member of the device and showing an alternative locking member at terminus of the U-shaped member, the second end of the device.

In operation, the first end (12) of device (10) is positioned such that the first end opening (44), which is defined in the first end (12), is sized and configured to be positioned at least partially around the male end (30) of the first connector (26) and interposed between the the first connector retaining structure (36) and the first end of the first tubular structure (16). The first end (12) of the device (10) can be configured to provide an annular ring around the male end (30) of the first connector (26) and as such, can be retained in its position as sandwiched between the first connector (26) and the first tubular structure (16). Alternatively, the first end opening (44) can be configured as an open ended or partial annular ring having a "U" or "modified-U" shape that is sized and configured to releasably snap fit around the male end (30) of the first connector (26). If so configured with a "U" shape or "modified-U" shape, the first end (12) of the device (10) can be slipped into the operating position interposed between the first connector (26) retaining structure (36) and the first tubular structure (16) and be retained in that operating position by a locking member (46) located on the device (10). In the exemplary embodiment shown in FIGS. 1, 3, 4, 5, and 6, such locking members (46) can be one or more extensions or nubs that serve to restrict the ease of movement of the device (10) from the operating position. These locking members (46) in the present example can be sized and configured to fit into receiving recesses (48) that are appropriately positioned on the adjacent first connector retaining structure (36). Variations of the locking members (46), to include revering the position of the extensions (46) and the receiving recesses (48) is fully within the scope of the present invention. It is even within the scope of the present invention that no receiving recesses (48) may be necessary and the locking members or nubs (46) can be positioned on the device (10) such that when the device is positioned for operation, the extensions or nubs (46) precisely fall into position along immediately adjacent to the edge of the retaining structure (36). The resilient quality of the device (10) is important to the function of the locking members or to the use of an alternative embodiment wherein a "modified-U" shape is snap-fitted around a portion of the male end (30) of the first connector (26). Another alternative embodiment of the locking members (46) that can be employed with the device (10) is shown in FIG. 2, where the modified-U shape terminates at each end of the "U" with an inwardly directed protrusion (46'), which serves to catch around the circumference of the second tubular structure (22). In such an embodiment, the resiliency of the material used to produce the device (10) is essential to allow the "U" shape to expand slightly as it passes around the second tubular structure (22) and then snap back into position to provide a releasable locking mechanism for the second end (18) of the device (10) in its operating position around the second tubular structure (22).

When in operation, the second end (18) of device (10) is positioned such that the second end opening (50), which is defined in the second end (18), is sized and configured to be positioned at least partially around the second tubular structure (22) and immediately adjacent and in contact with the retaining structure (52) of the second connector (42). This retaining structure (52) of the second connector 42) is, similar to the retaining structure (36) of the first connector (26), configured as an annular ring that at least partially surrounds the second tubular structure (22). The retaining structure (52) of the second tubular structure (22) is positioned along the length of the second connector at a position proximate to the male end (40) of the second connector (42). The precise position of the retaining structure (52) of the second connector (22) is generally standardized for breathing systems. For this reason, the size of the device (10) and particularly, the length or span of the bridging member (24) of the device (10) should be sufficient to promote a snug fit for the first end (12) of the device against the retaining structure (36) of the first connector (26) and a snug fit of the second end (18) of the device (10) against the retaining structure (52) of the second connector (42).

The resilient character of the material used in the manufacture of the device (10) permits the user to manually increase the distance separating the first end (12) form the second end (18) of the device (10). By manually increasing that distance, the device (10) is temporarily configured to easily slide into its operating position. The intermediate configuration of the device during the time when the user is moving it into the operating position is shown in FIG. 5. The device (10) when fully engaged with the first connector (26) and second connector (42) is shown in FIG. 4.

Figure 4:
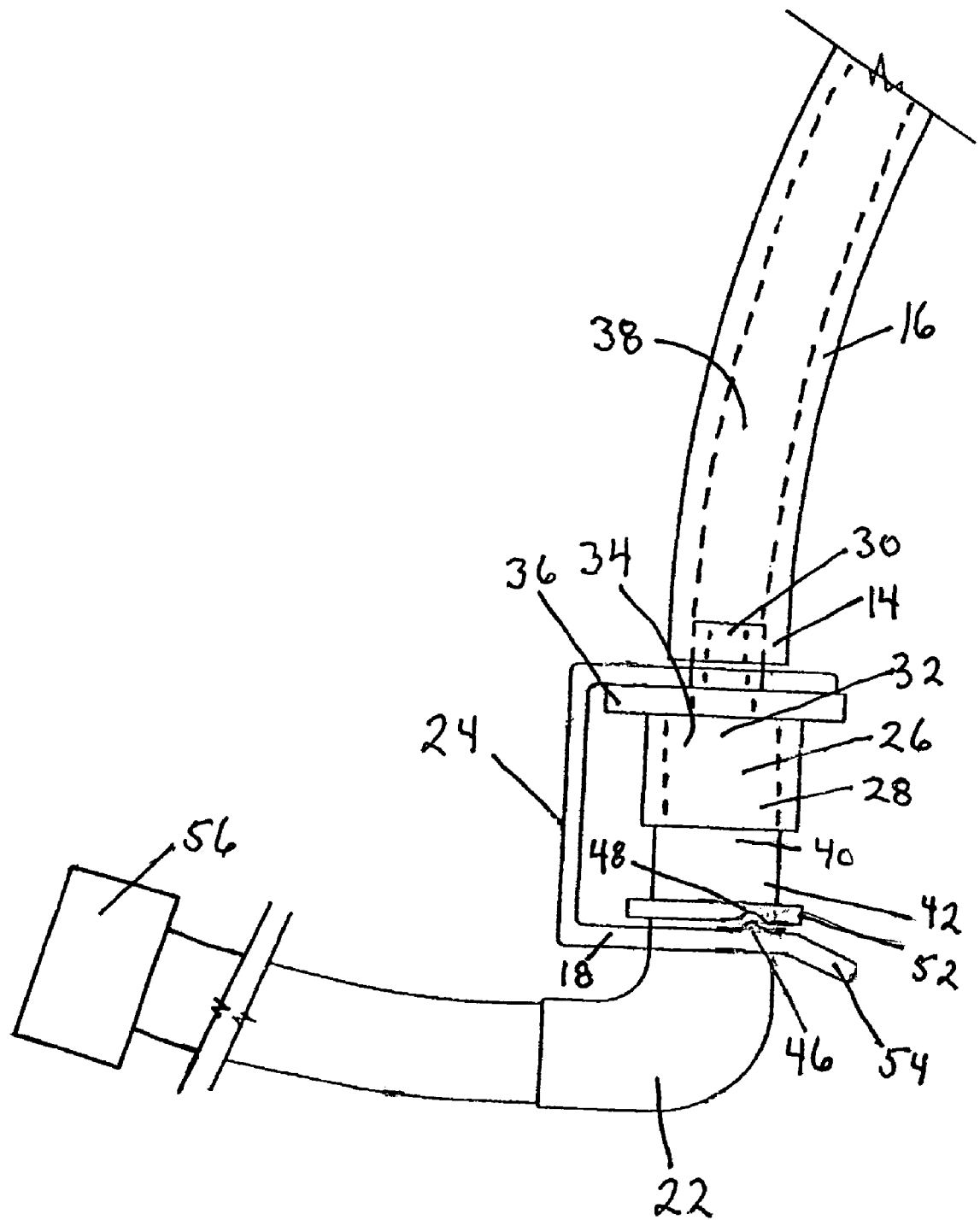
FIG. 4 provides a planar view of the device in its operation arrangement with two tubular structures joined together by a male-to-female connector assembly, the connection being connectable to a breathing system.
Figure 5:
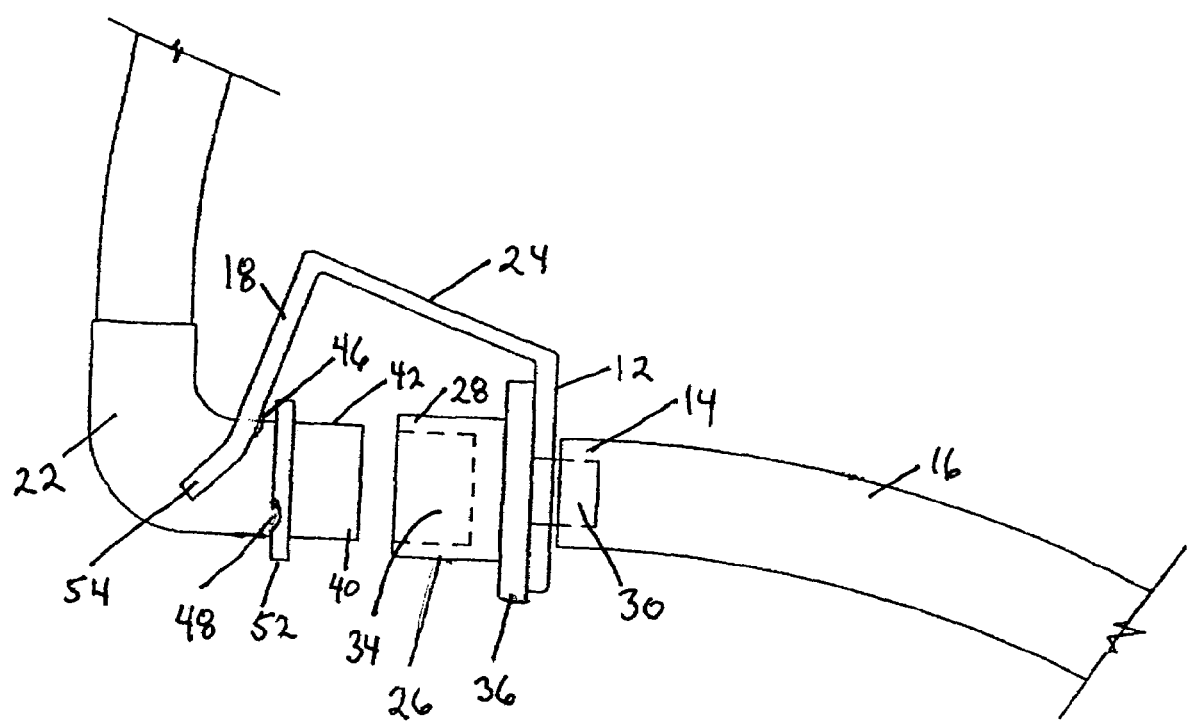
FIG. 5 provides a planar view of the device shown in FIG. 4 in an intermediate position of operational assembly. The device of the present invention is shown with the resilient material of the invention manually and temporarily distorted to increase the distance between the two ends of the device so as to permit connection of the two tubular structures.
Figure 6:
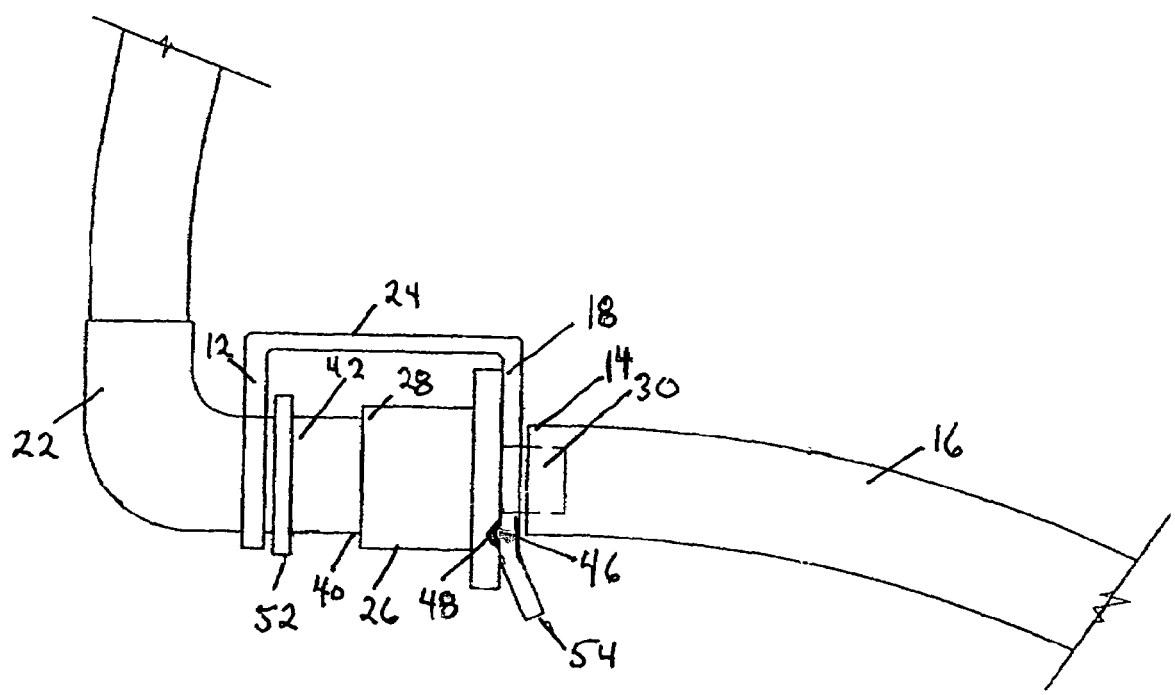
FIG. 6 provides an alternative operational assembly of the device with the two tubular structures using the circular or closed first end of the device positioned on the opposite tubular structure to that earlier shown.

When positioned in the releasably locked operating position, the device (10), as shown in FIG. 4, provides an inwardly directed bias that serves to hold the male end (54) of the second connector (42) in secure attachment to the of receiving female end (28) of the first connector (26). A grasping element (54) can be provided along the open edge of the second end (18) of the device (10) to facilitate the user function of manually opening or expanding of the distance between the first end (12) and second end (18) of the device (10) during the operation position of the device (10). This same grasping element (54) can serve to facilitate removing the device (10) from the operational position in contact with the first and second connectors (26, 42) as shown in FIG. 4. Once the device (10) is removed from its operational attachment to the second connector (42), it would be possible for the user to manually separate the male-to-female connection of the second connector (42) to the first connector (26). However, until the device is removed by the user, it serves to hold the two connectors (26, 42) in their male-to-female connection and protects against the hazard of an inadvertent disconnection.

Figure 3:
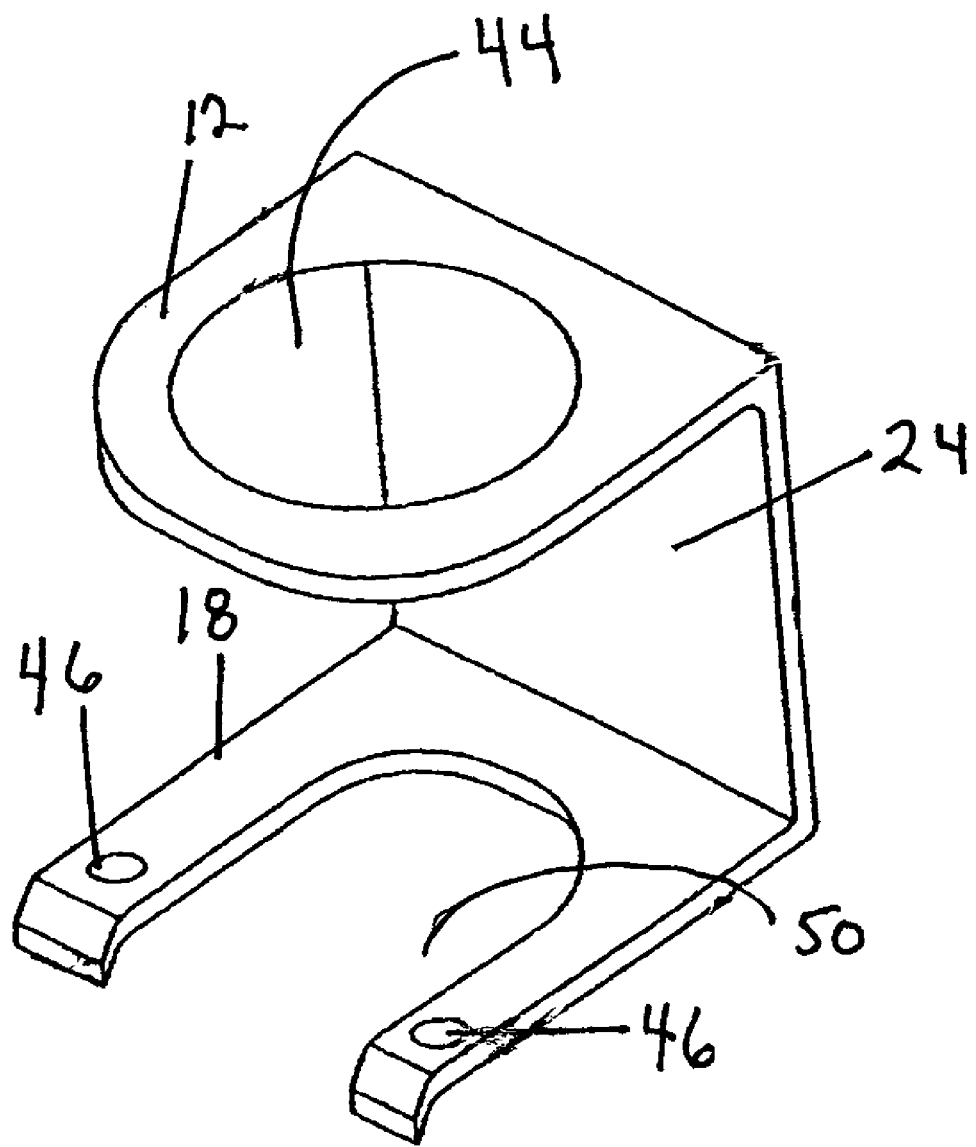
FIG. 3 provides a perspective view of the device of the present invention as seen from the underside of the bridging member of the device and showing an alternative locking member as well as an embodiment of the grasping element provided at the terminus of the U-shaped member, the second end of the device.
Figure 7:
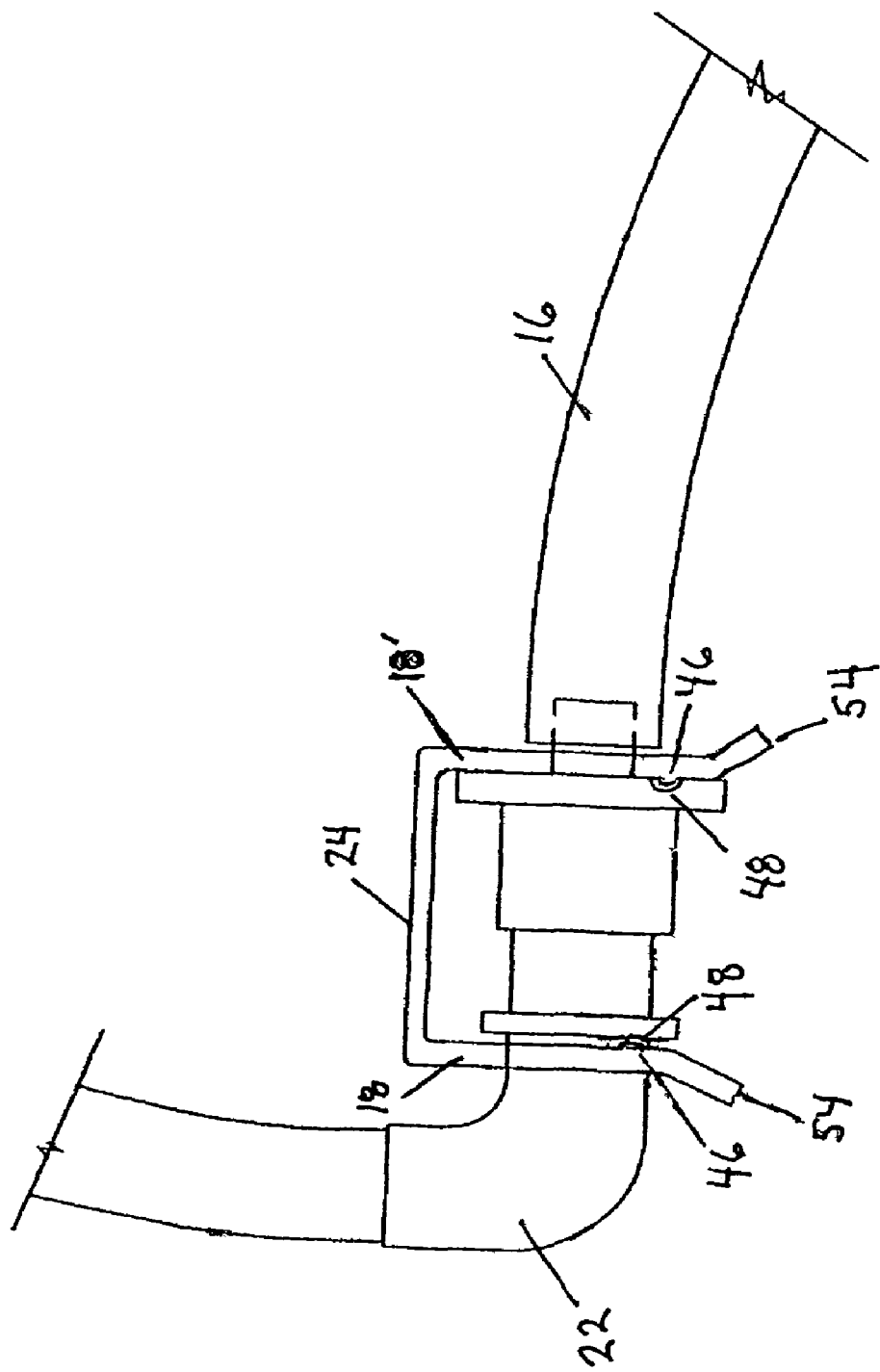
FIG. 7 provides a planar view of an alternative embodiment of the device of present invention in which both the first and second end of the device are configured in a similar open ended design, each end having similar locking members and grasping elements.

The above described example of the device (10) and its operation in releasably securing the connection of two tubular structures and their respective connectors is not limiting to the broad concept of the invention. As shown in FIG. 7, it is entirely within the scope of the invention to configure both the first end (12) and the second end (18) of the device (10) to have similar or identical structures; for example both ends of the device structured can have an open "U-shaped" or "modified U-shaped" structure as is described above for the second end (18) of device (10) and as shown in FIGS. 2 and 3. Such an approximate mirror-image design of the device (10) would, in view of the above provided description of the second end (18) of the device (10) result in a device (10) having two almost identical "second ends", designated in FIG. 7 as element (18) and element (18'). The variance between the two can be attributed primarily to size or proportion differences, which would be necessary to properly fit on the first (26) or second (42) connectors, respectively. Such an embodiment would allow the device (10) to be easily snapped into place over the joined first connector (26) and second connector (42) without the necessity of interposing the earlier described first end (26) circumferentially around the male end (30) of the first connector (26) before it is inserted into the lumen of the first tubular structure (16) as shown in FIGS. 1, 4, 5, and 6. In such an alternative embodiment, the device (10) can be manufactured in varying sizes and with modified-to-fit first and second connectors (26, 42) so as to provide a reliable securing device for many different applications.

As earlier indicated, the material of the device (10) can be any strong, resilient material that provides the necessary shape memory to permit the device to be distorted during the assembly and disassembly process on the tubular connectors. The device can be manufactured by any known means such as stamping, machining, molding, or any other method of manufacture adaptable to the structuring of the of the device (10).

The device of the present invention can be provided to the user as a component of a tubular assembly, such as an endotracheal tube. It is within the concept of this invention to provide an endotracheal tube having a releasable locking device for ensuring security of tubular connections. The structure and manufacture of endotracheal tubes is well described in U.S. Pat. No. 6,761,171 issued to Toti et al. on Jul. 13, 2004 and in U.S. Pat. No. 6,055,984 issued to Brain on May 2, 2000, the complete disclosures of which are fully incorporated herein by reference.

It is further within the concept of the present invention to provide a breathing system (56), as represented in FIG. 4, having a releasable locking device for ensuring security of tubular connections. The structure and manufacture of breathing systems or ventilating systems is well described in U.S. Pat. No. 6,761,165 issued to Strickland et al. on Jul. 13, 2004 and in U.S. Pat. No. 5,388,575 issued to Taube on Feb. 14, 1995, the complete disclosures of which are fully incorporated herein by reference.

The present invention can also be provided as an individual locking device that can be provided in different sizes and configurations as a lone item or as part of a kit that can be employed with any tubular connection assembly.

The concept of the present invention is not limited to tubular connections related to the movement of gases through connected tubular conduits but can be applied to the security of any tubular connection for the passage of any fluid.

The above description is provided as non-limiting examples of the present invention, which is limited only by the claims attached hereto.

What is claimed is:

1. A tubular connection releasable locking device comprising:
   a first end sized and configured to attach at or near the terminus of a first tubular structure;
   a second end sized and configured to attach at or near the terminus of a second tubular structure, said second end being sized and configured to have a modified "U"shape such that said second end can be positioned around at least a portion of said second tubular structure, said "U" shape being substantially perpendicular to the longitudinal axis of said second tubular structure;
   at least one releasable locking member, said locking member being located on at least one of said first and second ends of said device;
   a bridging member connecting said first end to said second end, said device being manufactured of a resilient material having strength and shape retention memory and said first end and said second end being disposed in relative opposition one to the other such that two complementary connectors, each associated with one of said first or second tubular structures, can be connected one to the other so as to provide a connection between said tubular structures and said device being sized and configured to exert a bias holding said two connectors in a secure connected relationship one with the other, wherein said device is positioned on said two complementary connectors such that said first end of said device is sized and configured as an annular ring, which fits circumferentially around said first connector, said first connector extending from a breathing system, and said second end of said device being positioned around at least a portion of said second connector, said second connector being an endotrachael tube assembly.

2. The device of claim 1, further comprising at least one grasping element attached to the edge of at least said second end of said device and configured to provide a grasping assist to a user for positioning or removing said device from a tubular connection assembly.

3. The device of claim 1, wherein said first and second ends of said device are similar in structure in that each is configured in a modified "U" shape so as to be easily placed in said positions to secure the connection between said first and second connectors.

4. An endotrachael tube comprising:
   an endotrachael tube manufactured and configured for medical use in ventilation of a subject, and
   a releasable locking device, comprising:
   a first end sized and configured to attach at or near the terminus of said endotrachael tube;
   a second end sized and configured to have a modified "U" shape such that said second end can be attached at one or near the terminus of a second tubular structure, said "U" shape being substantially perpendicular to the longitudinal axis of said second tubular structure, said second tubular structure being a ventilation tube extending from a breathing system or ventilator;
   at least one releasable locking member, said locking member being located on at least one of said first and second ends of said device;
   a bridging member connecting said first end to said second end, said device being manufactured of a resilient material having strength and shape retention memory and said first end and said second end being disposed in relative opposition one to the other such that two complementary connectors, each associated with one of said first or second tubular structures, can be connected one to the other so as to provide a connection between said endoscopic tube and said breathing system tube and said device being sized and configured to exert a bias holding said two connectors in a secure connected relationship one with the other.

5. A breathing system comprising:
   a breathing system or ventilator system; and
   a releasable locking device comprising:
   a first end sized and configured to attach at or near the terminus of an endoscopic tube;
   a second end sized and configured to have a modified "U" shape such that said second end can be attached at or near the terminus of a second tubular structure, said "U" shape being substantially perpendicular to the longitudinal axis of said second tubular structure, said second tubular structure being a hose or connector extending from said breathing system for connection to said endotrachael tube;
   at least one releasable locking member, said locking member being located on at least one of said first and second ends of said device;
   a bridging member connecting said first end to said second end, said device being manufactured of a resilient material having strength and shape retention memory and said first end and said second end being disposed in relative opposition one to the other such that two complementary connectors, each associated with one of said endotrachael tube or said second tubular structure can be connected one to the other so as to provide a connection between said tubular structures and said device so sized and configured to exert a bias holding said two connectors in a secure connected relationship one with the other.

6. A tubular connection kit for use with a breathing system, the kit comprising:
   at least one device as described in claim 1;
   at least one endotrachael tube; and
   a sterile container for enclosing said at least one endotrachael tube and said device.

7. A method of manufacturing a device for use as a releasable locking mechanism for a tubular connection, the method comprising:
   providing a strong resilient material having shape memory and forming said material to conform to the device as described in claim 1.

8. A method of manufacturing an endotrachael tube, having a releasable secure tubular connection locking system, the method comprising:
   manufacturing an endotrachael tube, having a first end or machine end,
   providing a device according to in claim 1; and
   connecting said device at or proximate to said machine end of said endotrachael tube to produce said endotrachael tube having a securing device for securing the connection between said endotrachael tube and a breathing system.

9. A method of manufacturing a breathing system having a releasable secure tubular connection locking system, the method comprising:
   manufacturing a breathing system having a tubular structure designed to attach directly or indirectly through a connector to an endotrachael tube or endotrachael tube connector;
   providing a device according to in claim 1; and
   connecting said device combining said breathing system with said device to produce said breathing system having a device for securing the connection between an endotrachael tube and said breathing system.

* * * * *